United States Patent [19]

Tsuruta et al.

[11] Patent Number: 4,952,266

[45] Date of Patent: Aug. 28, 1990

[54] METHOD OF ASSEMBLING CHEMICAL ANALYSIS SLIDE

[75] Inventors: Hikaru Tsuruta; Yuzo Tsunekawa, both of Kanagawa; Yoshinao Torii, Saitama, all of Japan

[73] Assignee: Fuji Photo Film Co., Ltd., Kanagawa, Japan

[21] Appl. No.: 241,450

[22] Filed: Sep. 8, 1988

[30] Foreign Application Priority Data

Sep. 8, 1987 [JP] Japan ................................ 62-224877

[51] Int. Cl.$^5$ ............................................. B29C 47/06
[52] U.S. Cl. ............................ 156/243; 156/244.11; 156/244.19; 156/244.22; 156/244.25; 422/60; 422/63; 422/66
[58] Field of Search ....................... 156/244.11, 244.19, 156/244.22, 244.25, 243; 422/56, 57, 60, 63, 66

[56] References Cited

U.S. PATENT DOCUMENTS 4,230,757 10/1980 Toner ..................................... 422/56
4,437,970 3/1984 Kitajima et al. ..................... 204/412
4,521,359 6/1985 Tsien .............................. 156/244.11

Primary Examiner—Caleb Weston
Attorney, Agent, or Firm—Sughrue, Mion, Zinn, Macpeak & Seas

[57] ABSTRACT

A dry type chemical analysis slide has a plurality of plate members formed of thermoplastic resin and a mount which holds a detecting element formed by the use of an electrode film and is integrally sandwiched between the plate members. At least one of the plate members is formed by extrusion.

2 Claims, 4 Drawing Sheets

U.S. Patent   Aug. 28, 1990   Sheet 4 of 4   4,952,266 ly to a method of assembling a chemical analysis slide having dry ion selective electrodes for electrically or optically quantifying metabolites, metabolism promoters or antimetabolites in body fluid such as blood.

METHOD OF ASSEMBLING CHEMICAL ANALYSIS SLIDE

BACKGROUND OF THE INVENTION

1. Field of the Invention

This invention relates to a method of assembling a chemical analysis slide for analyzing concentration or activity of specific ions in a liquid, and more particularly to a method of assembling a chemical analysis slide having dry ion selective electrodes for electrically or optically quantifying metabolites, metabolism promoters or antimetabolites in body fluid such as blood.

2. Description of the Prior Art

As an instrument for measuring concentration or activity of specific ions in a solution, there has been known a chemical analysis slide having dry ion selective electrodes which is easy to control, provides facility for measurement and can be produced at low cost.

The chemical analysis slide disclosed in Japanese Unexamined Patent Publication No. 58(1983)-211648, which corresponds to U.S. Pat. No. 4,437,970, comprises electrodes, an adhesive double-coated tape, a distributor member and the like sandwiched between upper and lower frames and bonded thereto.

In such a chemical analysis slide, a plurality of electrodes are provided in parallel laterally spaced from each other in order to enable measurement for a plurality of ions. The electrodes are generally accommodated in respective recesses formed in the upper frame or the lower frame so that evenness of the outer surfaces of the slide and the integrality of the slide are ensured. The frame provided with the recesses for accommodating the electrodes is generally formed by injection molding.

Further, we have proposed a method of making a frame having a desired shape by laminating a plurality of plastic hoops in Japanese Patent Application No. 61(1986)-164569.

However the method of assembling the chemical analysis slide in which the frame is made by injection molding is disadvantageous in that improvement in productivity is inherently limited and the assembling cost of the slide cannot be substantially reduced.

On the other hand, said method of making the frame by laminating a plurality of plastic hoops is superior to the preceding method in that the assembling cost can be better reduced. However, with this method, remarkable cost reduction cannot be expected since differently shaped hoops, e.g., a hoop with an opening and a hoop without opening must be laminated, thereby increasing the manhours required in assembly. Further, the increase in the manhours adversely affects the working stability of the assembling machine.

SUMMARY OF THE INVENTION

In view of the foregoing observations and description, the primary object of the present invention is to provide a method of assembling a chemical analysis slide which can remarkably lower the assembling cost of the chemical analysis slide and ensure an excellent working stability of the assembling machine.

In accordance with the present invention, there is provided a method of assembling a dry type chemical analysis slide having a plurality of plate members formed of thermoplastic resin and a mount which holds a detecting element formed by the use of an electrode film and is integrally sandwiched between the plate members, characterized in that at least one of the plate members is formed by extrusion.

By use of extrusion, a plate member in a continuous length having a regular cross-sectional shape can be molded with ease, and the individual plate members can be mass-produced by cutting the plate member in a continuous length while conveying it in the longitudinal direction. Thus the assembling cost can be markedly lowered as compared with the case where the plate members are injection-molded. Further, unlike the case where the plate members are formed by laminating hoops, the manhours required for laminating the hoops and the like are not necessary, whereby the assembling manhours can be reduced and the working stability of the assembling machine can be improved.

DESCRIPTION OF THE PREFERRED EMBODIMENT

Figure 5:
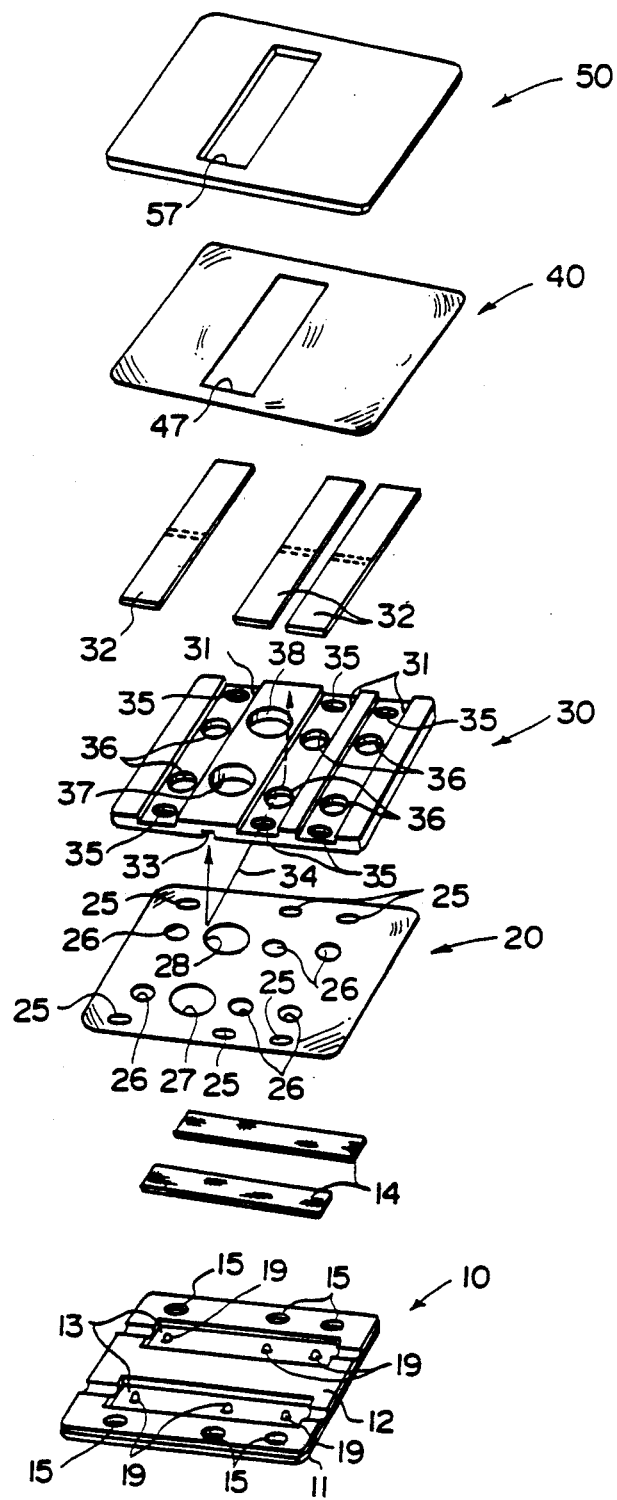
FIG. 5 is an exploded perspective view showing the chemical analysis slide formed by the procedure shown in FIG. 4.

In FIG. 5, an example of the chemical analysis slides which can be assembled in accordance with the method of the present invention comprises a lower cover member 10, an intermediate frame member 30 laminated to the lower cover member 10 with a first adhesive double-coated tape 20 intervening therebetween and an upper cover member 50 laminated to the intermediate frame member 30 with a second adhesive double-coated tape 40 intervening therebetween. The lower cover member 10 is formed by laminating first and second plate members 11 and 12 with an adhesive double-coated tape (not shown). The second plate member 12 is provided with a pair of elongated openings, whereby a pair of spreader cloth receiving recesses 13 are formed in the lower cover member 10. A pair of spreader cloths 14 are respectively received in the spreader cloth receiving recesses 13. Probe insertion holes 15 are formed in the lower cover member 10 through the first and second plate members 11 and 12. A plurality of projections 19 are formed in the first plate member 11 to project into the spreader cloth receiving recesses 13. The first adhesive double-coated tape 20 is provided with probe insertion holes 25 in alignment with the probe insertion holes 15 of the lower cover member 10. The first double-sided adhesive tape 20 is further provided with liquid rising holes 26, a sample liquid supply hole 27 and a control liquid supply hole 28. The intermediate frame member 30 is provided with three electrode receiving recesses 31 extending in parallel to each other, and probe insertion holes 35, liquid rising holes 36, a sample liquid supply hole 37 and a control liquid supply hole 38 are formed in the electrode receiving recesses 31. Three ion selective electrodes 32 are respectively received in the electrode receiving recesses 31. The intermediate frame member 30 is further provided with a bridge receiving groove 33 on the lower side thereof and a bridge thread 34 is welded in the bridge receiving groove 33. The second adhesive double-coated tape 40 are provided with a rectangular opening 47 and the upper cover member 50 is provided with a rectangular opening 57. In the assembled state, the probe insertion holes 15, 25 and 35 of the lower cover member 10, the first adhesive double-coated tape 20 and the intermediate frame member 30 are aligned with each other to give access to the ion selective electrodes 32 in the electrode receiving recesses 31 of the intermediate frame member 30. Further, the sample liquid supply holes 27 and 37 of the first adhesive double-coated tape 20 and the intermediate frame member 30 are in alignment with each other and with one of the spreader cloths 14 in the spreader cloth receiving recesses 13 in the lower cover member 10. Similarly, the control liquid supply holes 28 and 38 are in alignment with each other and with the other spreader cloth 14. The rectangular openings 47 and 57 of the second double-sided adhesive tape 40 and the upper cover member 50 are in alignment with each other, and cover both the aligned sample liquid supply holes and the aligned control liquid supply holes to give access thereto. The liquid rising holes 26 and 36 of the first adhesive double-coated tape 20 and the intermediate frame member 30 are aligned to form passage through with liquid supplied to the spreader cloth 14 rises to the electrodes 32.

In accordance with the method of the present invention, at least one of the first plate member 11, the second plate member 12, the intermediate frame member 30 and the upper cover member 50 is formed by extrusion. Now, the method of the present invention will be described with reference to FIGS. 1 to 4 on the basis of a case where only the intermediate frame member 30 is formed by extrusion.

Figure 1:
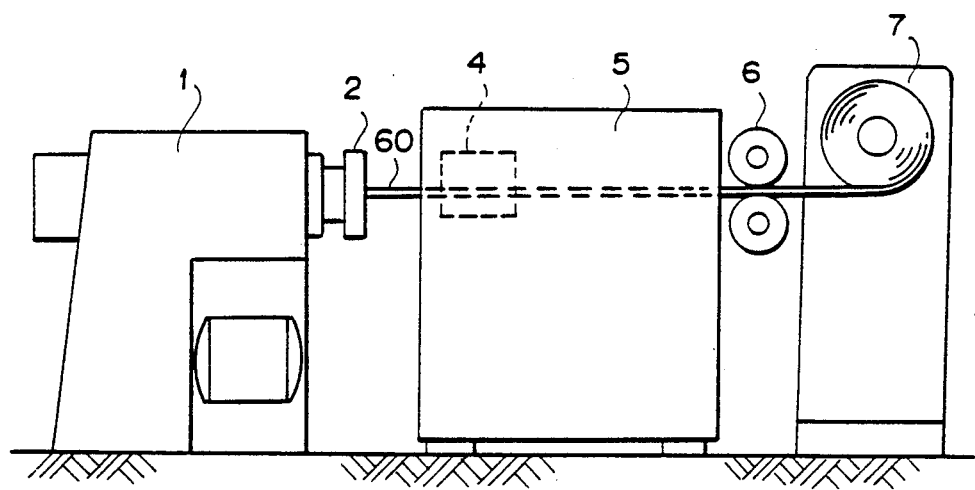
FIG. 1 is a side view showing an extruder for carrying out the method of the present invention.
Figure 2:
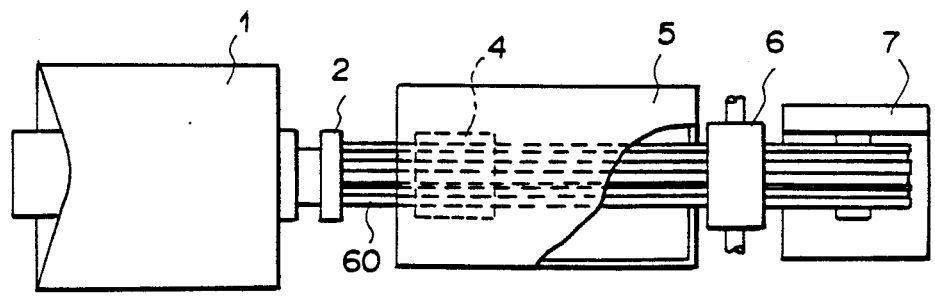
FIG. 2 is a plan view of the extruder.
Figure 3:
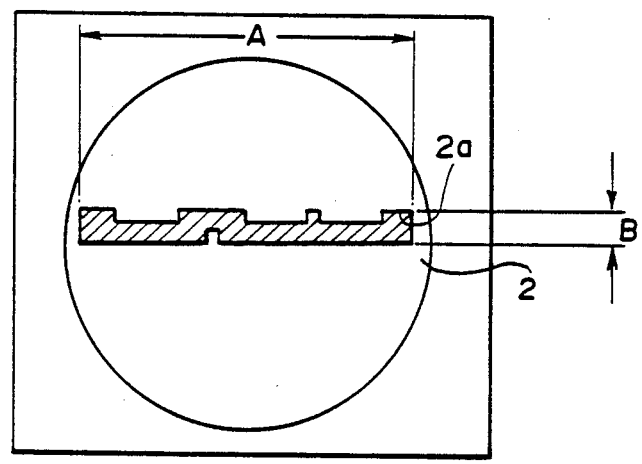
FIG. 3 is a schematic view showing the extrusion orifice of the extruder.

In FIG. 1, an extruder has an extruder head 1 and an extruder die 2 having an extrusion orifice 2a shown in FIG. 3 is mounted on the extruder head 1. Plastic material extruded through the die 2 is formed into a continuous plate member 60 having a cross-sectional shape conforming to the shape of the extrusion orifice 2a. The extrusion orifice 2a is shaped to provide the extruded continuous plate member 60 with a groove on one side and three recesses on the other side which respectively correspond to the three electrode receiving recesses 31 and the bridge receiving groove 33 of the intermediate frame member 30. The continuous plate member 60 is suitably sized by a sizing system 4, cooled at a cooling system 5, is fed by a take-off system 6 and is taken up by a take-up system 7. Otherwise, the continuous plate member 60 may be cut into desired lengths and piled up. The size of the extruder head 1 may be determined according to the size of the continuous plate member 60 to be formed. For example, the extruder screw may be 40 to 60 mm in diameter. The extrusion orifice 2a may be 30 to 70 mm in width A and 0.5 to 2.0 mm in thickness B. The cooling system 5, the take-off system 6 and the take-up system 7 may be of the known structure and will not be described here. The plastic material may of any kind so long as the flow properties thereof conform to the cross-sectional shape of the flat plate member 60. In the case where the cross-section of the plate member 60 is complicated in shape, PVC, ABS or polystyrene is generally preferable. It is preferred that the melt index of the plastic material be 1 to 5 g. With such a melt index, accuracy within $\pm 1\%$ can be obtained in the direction of the width, and accuracy within $\pm 3\%$ can be obtained in the direction of the thickness.

Figure 4:
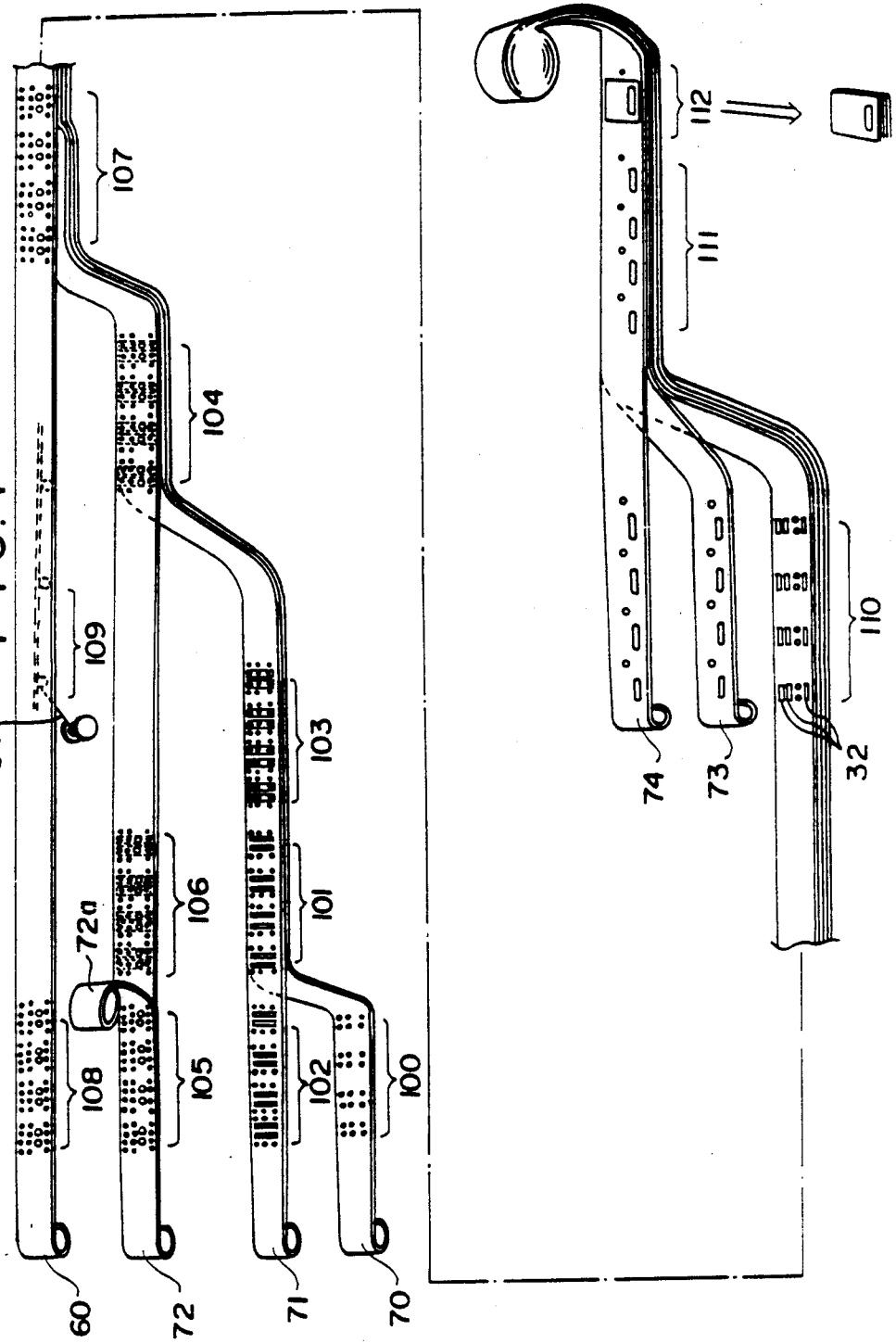
FIG. 4 is a schematic perspective view showing procedure of assembling chemical analysis slides using the continuous plate formed by the extruder.

FIG. 4 shows the procedure of assembling chemical analysis slides such as shown in FIG. 5 using the continuous plate member 60 formed by the extruder. In FIG. 4, reference numeral 70 denotes 0.2 mm thick polystyrene strip in a continuous length for forming said first plate member 11 of the lower cover member 10. Reference numeral 71 denotes 0.3 mm thick polystyrene strip in a continuous length provided with an adhesive double-coated tape (not shown) on the lower surface thereof. The strip 71 is for forming the second plate member 12 of the lower cover member 10. Reference numeral 72 denotes 0.1 mm thick adhesive strip in a continuous length for forming said first adhesive double-coated tape 20. The strip 72 is provided with release paper 72a on the upper surface. Reference numeral 60 denotes 1.2 mm thick polystyrene strip in a continuous length for forming said intermediate frame member 30. The strip 60 is formed by extrusion described above with reference to FIGS. 1 to 3, and accordingly has three recesses or grooves forming the electrode receiving recesses 31 on the upper surface and a single groove forming the bridge receiving groove 33, though the recesses and the groove are not shown in FIG. 4 for the purpose of simplicity. Reference numeral 73 denotes 0.1 mm thick adhesive strip for forming said second adhesive double-coated tape 40. Reference numeral 74 denotes 0.2 mm thick polystyrene strip in a continuous length for forming said upper cover member 50.

The strips 60 and 71 to 74 are longitudinally unwound and conveyed in parallel by suitable means, while formed with required openings and laminated together, and individual chemical analysis slides are stamped out from the laminated strips. The strip 70 is first formed with a plurality of openings for forming the probe insertion holes 15 at a stamping station 100 and conveyed to a laminating station 101. The strip 71 is formed with a plurality of openings for forming the probe insertion holes 15 and the spreader cloth receiving recesses 13 in a predetermined pattern at a stamping station 102 and conveyed to the laminating station 101, where the strips 70 and 71 are thermowelded together with the openings for forming the probe insertion holes 15 aligned with each other. Then the laminated 70-71 strip assembly is conveyed to an embossing station 103 where the strip 70 is formed with a plurality of projections (corresponding to said projections 19). Thereafter the laminated 70-71 strip assembly is conveyed to a laminating station 104. The strip 72 is formed with a plurality of openings for forming said probe insertion holes 25, the liquid rising holes 26, the sample liquid supply hole 27 and the control liquid supply hole 28 at a stamping station 105, and then conveyed to a thermowelding station 106 after the releasing paper 72a is removed. At the thermowelding station 106, a pair of spreader cloths are bonded to the lower surface of the strip 72 in a predetermined position. Thereafter the strip 72 provided with the spreader cloths is conveyed to the laminating station 104, where the strip 72 is laminated to the strip 71 with the openings for forming probe insertion holes 15 and 24 aligned with each other and the spreader cloths positioned in the respective spreader cloth receiving recesses in the laminated 70-71 strip assembly. Then the laminated 70-71-72 strip assembly thus formed is conveyed to a laminating station 107. The strip 60 is formed with a plurality of openings for forming the probe insertion holes 35, the liquid rising holes 36, the sample liquid supply hole 37 and the control liquid supply hole 38 at a stamping station and then bridge thread 34 is ultrasonically welded to the groove for forming the bridge receiving groove 33 at a bridge welding station 109. Then the strip 60 is laminated to the strip 72 at the laminating station 107 with the openings for forming the probe insertion holes 25 and 35, the liquid rising holes 26 and 36, the sample liquid supply holes 27 and 37 and the control liquid supply holes 28 and 38 in the respective strips aligned with the corresponding openings in the other strip. Then the laminated 70-71-72-60 strip assembly thus formed is conveyed to an electrode setting station 110, and ion selective electrodes 32 are inserted into the recesses of the strip 60. The laminated 70-71-72-60 strip provided with the electrodes is conveyed to a laminating station 111 and the strips 73 and 74 respectively formed with openings for forming said openings 47 and 57 are laminated to the strip 60. Thereafter individual chemical analysis slides are stamped out at a stamping station 112.

Though, in the embodiment described above, only the strip 60 for forming the intermediate frame member 30 is formed by extrusion, other strips may also be formed by extrusion. Further, the extruded strip may be processed after extrusion. For example, the extruded strip may be processed with a heat-insulated embossing roll.

We claim:

1. A method of assembling a dry type chemical analysis slide having a plurality of plate members formed of thermoplastic resin and a mount which holds a detecting element formed by the use of an electrode film and is integrally sandwiched between the plate members, said method comprising the following steps:
   (a) forming at least one of the plate members by extrusion into a continuous strip with a plurality of recesses on one side which respectively correspond to electrode receiving recesses of said at least one plate member;
   (b) winding up the continuous strip into a roll;
   (c) longitudinally unwinding and conveying said extruded continuous strip member in parallel with a plurality of other continuous strips which correspond to the other of said plurality of plate members while forming any required openings therein;
   (d) laminating said extruded continuous strip and said plurality of other continuous strips together so as to form a single laminated strip; and
   (e) stamping out individual chemical analysis slides from said laminated strip.

2. A method of forming a dry type chemical analysis slide according to claim 1, wherein said extrusion step (a) includes forming said plurality of recesses on an upper surface of said continuous strip and forming a single bridge receiving groove on a lower surface thereof.

* * * * *